United States Patent
Singla et al.

(10) Patent No.: US 11,890,234 B2
(45) Date of Patent: Feb. 6, 2024

(54) PATIENT TRANSPORT APPARATUS WITH CRASH DETECTION

(71) Applicant: Stryker Corporation, Kalamazoo, MI (US)

(72) Inventors: Neeraj Singla, Portage, MI (US); Aaron Douglas Furman, Kalamazoo, MI (US); Bhavin Rajeshkumar Kapadia, Portage, MI (US); Brandon David Naber, Portage, MI (US); Thomas Alan Puvogel, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 549 days.

(21) Appl. No.: 17/131,933

(22) Filed: Dec. 23, 2020

(65) Prior Publication Data

US 2021/0196534 A1    Jul. 1, 2021

Related U.S. Application Data

(60) Provisional application No. 62/954,855, filed on Dec. 30, 2019.

(51) Int. Cl.
*A61G 1/04* (2006.01)
*G01P 15/02* (2013.01)
(Continued)

(52) U.S. Cl.
CPC ............... *A61G 1/04* (2013.01); *G01P 15/02* (2013.01); *G01S 19/42* (2013.01); *G16H 40/40* (2018.01);
(Continued)

(58) Field of Classification Search
CPC .. A61G 1/04; A61G 2203/30; A61G 2203/72; A61G 3/0816; G01P 15/02;
(Continued)

(56) References Cited

U.S. PATENT DOCUMENTS

| 5,210,476 A | * | 5/1993 | Kazato | ............... | G05B 19/4062 318/560 |
| 5,645,667 A | | 7/1997 | Kusen | | |

(Continued)

FOREIGN PATENT DOCUMENTS

| CA | 2529091 A1 | 12/2003 |
| DE | 19505162 C1 | 3/1996 |

(Continued)

OTHER PUBLICATIONS

English language abstract for DE 195 05 162 C1 extracted from espacenet.com database on Jan. 8, 2021, 1 page.

(Continued)

*Primary Examiner* — Mussa A Shaawat
(74) *Attorney, Agent, or Firm* — Howard & Howard Attorneys PLLC (57) ABSTRACT

A patient transport apparatus with a support structure having a base, a support frame, and a patient support deck defining a support surface. An inertial sensor is coupled to the support structure and generates a signal representing a change in velocity of the support structure. A controller in communication with the inertial sensor has a processor and a non-transitory storage medium having stored thereon a program that monitors the signal generated by the inertial sensor for changes relative to a predetermined threshold. In response to an event in which the signal exceeds the predetermined threshold, the program is further configured to: generate a waveform based on the signal received from the inertial sensor; store the waveform at an overwritable address in the (Continued)

non-transitory storage medium; and generate an entry in an event log stored in the non-transitory storage medium, the entry comprising one or more parameters associated with the waveform.

20 Claims, 6 Drawing Sheets

(51) Int. Cl.
  *G01S 19/42* (2010.01)
  *G16H 40/40* (2018.01)
  *G16H 40/67* (2018.01)
  *G06Q 10/1093* (2023.01)
(52) U.S. Cl.
  CPC ..... *A61G 2203/30* (2013.01); *G06Q 10/1093* (2013.01); *G16H 40/67* (2018.01)
(58) Field of Classification Search
  CPC ..... G01P 15/0891; G01S 19/42; G16H 40/40; G16H 40/67
  See application file for complete search history.

(56) References Cited

U.S. PATENT DOCUMENTS

| | | | |
|---|---|---|---|
| 5,789,884 A * | 8/1998 | Hancock | G05G 7/00 |
| | | | 318/587 |
| 7,242,306 B2 | 7/2007 | Wildman et al. | |
| 7,398,571 B2 | 7/2008 | Souke et al. | |
| 7,887,113 B2 | 2/2011 | Lambarth et al. | |
| 8,155,918 B2 | 4/2012 | Reed et al. | |
| 8,439,416 B2 | 5/2013 | Lambarth et al. | |
| 8,634,981 B1 * | 1/2014 | Hyde | A61G 1/0275 |
| | | | 180/19.1 |
| 8,756,078 B2 | 6/2014 | Collins, Jr. et al. | |
| 9,056,556 B1 | 6/2015 | Hyde et al. | |
| 9,079,505 B1 | 7/2015 | Hyde et al. | |
| 9,269,990 B2 | 2/2016 | Andrieux et al. | |
| 9,307,033 B1 | 4/2016 | Meschkat | |
| 9,424,699 B2 | 8/2016 | Kusens et al. | |
| 9,466,163 B2 | 10/2016 | Kusens et al. | |
| 9,691,206 B2 | 6/2017 | Kusens et al. | |
| 9,774,991 B2 | 9/2017 | Kusens | |
| 9,838,836 B2 | 12/2017 | Hayes et al. | |
| 9,838,849 B2 | 12/2017 | Kusens | |
| 9,858,741 B2 | 1/2018 | Kusens et al. | |
| 9,892,310 B2 | 2/2018 | Kusens et al. | |
| 9,892,311 B2 | 2/2018 | Kusens et al. | |
| 9,916,649 B1 | 3/2018 | Kusens | |
| 9,984,521 B1 | 5/2018 | Kusens et al. | |
| 9,997,001 B2 | 6/2018 | Kusens et al. | |
| 9,998,857 B2 | 6/2018 | Kusens | |
| 10,010,042 B1 | 7/2018 | Lee et al. | |
| 10,013,831 B1 | 7/2018 | Kusens et al. | |
| 10,045,893 B2 * | 8/2018 | Childs | A61G 1/0237 |
| 10,085,905 B2 | 10/2018 | Bhimavarapu et al. | |
| 10,090,068 B2 | 10/2018 | Kusens et al. | |
| 10,096,101 B2 | 10/2018 | Kusens | |
| 10,109,179 B2 | 10/2018 | Kusens | |
| 10,115,253 B2 | 10/2018 | Kusens et al. | |
| 10,115,254 B1 | 10/2018 | Kusens et al. | |
| 10,121,299 B2 | 11/2018 | Kusens et al. | |
| 10,147,184 B2 | 12/2018 | Kusens et al. | |
| 10,147,256 B2 | 12/2018 | Kusens et al. | |
| 10,174,184 B2 | 1/2019 | Otake | |
| 10,187,755 B2 | 1/2019 | Kusens et al. | |
| 10,194,278 B1 | 1/2019 | Kusens | |
| 10,198,886 B2 | 2/2019 | Kusens et al. | |
| 10,210,378 B2 | 2/2019 | Kusens et al. | |
| 10,303,924 B2 | 5/2019 | Kusens et al. | |
| 10,388,016 B2 | 8/2019 | Kusens et al. | |
| 10,417,385 B2 | 9/2019 | Kusens et al. | |
| 10,504,226 B2 | 12/2019 | Kusens et al. | |
| 10,510,443 B2 | 12/2019 | Kusens et al. | |
| 10,514,288 B2 | 12/2019 | Droin et al. | |
| 10,521,989 B2 | 12/2019 | Kusens et al. | |
| 10,524,722 B2 | 1/2020 | Kusens et al. | |
| 10,603,234 B2 | 3/2020 | Puvogel et al. | |
| 10,643,061 B2 | 5/2020 | Kusens et al. | |
| 10,643,446 B2 | 5/2020 | Kusens et al. | |
| 10,650,117 B2 | 5/2020 | Kusens et al. | |
| 2002/0000727 A1 | 1/2002 | Rass et al. | |
| 2003/0183427 A1 * | 10/2003 | Tojo | A61G 5/1051 |
| | | | 180/8.1 |
| 2005/0113996 A1 | 5/2005 | Pillar et al. | |
| 2005/0236208 A1 * | 10/2005 | Runkles | B60K 17/303 |
| | | | 180/254 |
| 2006/0190176 A1 | 8/2006 | Gleacher et al. | |
| 2008/0312971 A2 | 12/2008 | Rosow et al. | |
| 2009/0088924 A1 | 4/2009 | Coffee et al. | |
| 2010/0039247 A1 | 2/2010 | Ziegler et al. | |
| 2011/0087416 A1 * | 4/2011 | Patmore | A61G 1/0287 |
| | | | 180/19.1 |
| 2011/0208541 A1 | 8/2011 | Wilson et al. | |
| 2014/0076644 A1 * | 3/2014 | Derenne | A61G 7/012 |
| | | | 180/19.2 |
| 2014/0090171 A1 * | 4/2014 | Hyde | G05D 1/0061 |
| | | | 701/2 |
| 2014/0094997 A1 * | 4/2014 | Hyde | G05D 1/0246 |
| | | | 348/148 |
| 2014/0297327 A1 | 10/2014 | Heil et al. | |
| 2015/0109442 A1 | 4/2015 | Derenne et al. | |
| 2015/0239365 A1 | 8/2015 | Hyde et al. | |
| 2016/0049028 A1 | 2/2016 | Kusens et al. | |
| 2016/0089283 A1 * | 3/2016 | DeLuca | A61G 7/08 |
| | | | 180/413 |
| 2016/0098676 A1 | 4/2016 | Kusens et al. | |
| 2016/0136018 A1 * | 5/2016 | DeLuca | A61G 1/0287 |
| | | | 5/611 |
| 2016/0180668 A1 | 6/2016 | Kusens et al. | |
| 2016/0183864 A1 | 6/2016 | Kusens et al. | |
| 2016/0247342 A1 | 8/2016 | Kusens et al. | |
| 2016/0259906 A1 | 9/2016 | Iucha et al. | |
| 2016/0366327 A1 | 12/2016 | Kusens | |
| 2016/0367415 A1 * | 12/2016 | Hayes | B60K 31/0008 |
| 2016/0371786 A1 | 12/2016 | Kusens et al. | |
| 2017/0055113 A1 | 2/2017 | Kusens | |
| 2017/0076526 A1 | 3/2017 | Kusens et al. | |
| 2017/0094477 A1 | 3/2017 | Kusens et al. | |
| 2017/0109770 A1 | 4/2017 | Kusens et al. | |
| 2017/0111770 A1 | 4/2017 | Kusens | |
| 2017/0116790 A1 | 4/2017 | Kusens et al. | |
| 2017/0193177 A1 | 7/2017 | Kusens | |
| 2017/0193180 A1 | 7/2017 | Kusens et al. | |
| 2017/0193279 A1 | 7/2017 | Kusens et al. | |
| 2017/0193772 A1 | 7/2017 | Kusens et al. | |
| 2017/0195637 A1 | 7/2017 | Kusens et al. | |
| 2017/0213445 A1 | 7/2017 | Kusens | |
| 2017/0281440 A1 * | 10/2017 | Puvogel | A61G 7/0527 |
| 2017/0287316 A1 | 10/2017 | Wildman et al. | |
| 2017/0352212 A1 | 12/2017 | Kusens et al. | |
| 2018/0040091 A1 | 2/2018 | Kusens | |
| 2018/0041864 A1 | 2/2018 | Kusens | |
| 2018/0084390 A1 | 3/2018 | Kusens | |
| 2018/0096550 A1 | 4/2018 | Kusens et al. | |
| 2018/0114053 A1 | 4/2018 | Kusens et al. | |
| 2018/0135987 A1 * | 5/2018 | Evans | G01C 21/20 |
| 2018/0137340 A1 | 5/2018 | Kusens et al. | |
| 2018/0151010 A1 | 5/2018 | Kusens et al. | |
| 2018/0167816 A1 | 6/2018 | Kusens et al. | |
| 2018/0189946 A1 | 7/2018 | Kusens et al. | |
| 2018/0211464 A1 | 7/2018 | Kusens et al. | |
| 2018/0218489 A1 | 8/2018 | Kusens | |
| 2018/0228676 A1 | 8/2018 | Merdek | |
| 2018/0232979 A1 | 8/2018 | Kusens et al. | |
| 2018/0232980 A1 | 8/2018 | Kusens et al. | |
| 2018/0247476 A1 | 8/2018 | Kusens et al. | |
| 2018/0252535 A1 * | 9/2018 | Bhimavarapu | G01S 5/0295 |
| 2018/0279075 A1 | 9/2018 | Kusens | |
| 2018/0293826 A1 | 10/2018 | Kusens et al. | |
| 2018/0300977 A1 | 10/2018 | Kusens et al. | |

(56) References Cited

U.S. PATENT DOCUMENTS

| | | | |
|---|---|---|---|
| 2018/0360681 A1* | 12/2018 | Paul | A61G 7/012 |
| 2018/0369035 A1* | 12/2018 | Bhimavarapu | A61G 7/018 |
| 2018/0376300 A1 | 12/2018 | Kusens et al. | |
| 2019/0006046 A1 | 1/2019 | Kusens et al. | |
| 2019/0019283 A1 | 1/2019 | Kusens | |
| 2019/0043192 A1 | 2/2019 | Kusens et al. | |
| 2019/0073849 A1 | 3/2019 | Kusens et al. | |
| 2019/0122028 A1 | 4/2019 | Kusens et al. | |
| 2019/0206218 A1* | 7/2019 | Kusens | G08B 21/0476 |
| 2019/0298229 A1* | 10/2019 | Kostic | A61B 5/6891 |
| 2019/0318478 A1 | 10/2019 | Kusens et al. | |
| 2020/0143643 A1 | 5/2020 | Kusens et al. | |
| 2020/0210679 A1 | 7/2020 | Kusens et al. | |
| 2020/0226636 A1 | 7/2020 | Kim | |
| 2020/0302462 A1 | 9/2020 | Kusens et al. | |

FOREIGN PATENT DOCUMENTS

| | | |
|---|---|---|
| DE | 10018560 A1 | 10/2001 |
| DE | 102008011899 A1 | 9/2009 |
| DE | 102010015736 A1 | 10/2010 |
| EP | 0727298 A1 | 8/1996 |
| EP | 0727298 B1 | 8/1999 |
| EP | 1146185 A2 | 10/2001 |
| EP | 1146185 A3 | 3/2003 |
| EP | 1146185 B1 | 6/2005 |
| WO | 2016025927 A1 | 2/2016 |
| WO | 2016049593 A1 | 3/2016 |
| WO | 2016049593 A4 | 5/2016 |
| WO | 2016200556 A1 | 12/2016 |
| WO | 2017027427 A1 | 2/2017 |
| WO | 2017031111 A1 | 2/2017 |
| WO | 2017058991 A1 | 4/2017 |
| WO | 2017070350 A1 | 4/2017 |
| WO | 2017058991 A4 | 5/2017 |
| WO | 2017070350 A4 | 7/2017 |
| WO | 2017124056 A1 | 7/2017 |
| WO | 2018026979 A1 | 2/2018 |
| WO | 2018236588 A2 | 12/2018 |
| WO | 2018236588 A3 | 1/2019 |

OTHER PUBLICATIONS

English language abstract for DE 100 18 560 a1 extracted from espacenet.com database on Jan. 8, 2021, 2 pages.

English language abstract and machine-assisted English translation for DE 10 2008 011 899 A1 extracted from espacenet.com database on Jan. 8, 2021, 9 pages.

English language abstract and machine-assisted English translation for DE 10 2010 015 736 A1 extracted from espacenet.com database on Jan. 8, 2021, 5 pages.

English language abstract for EP 0 727 298 A1 extracted from espacenet.com database on Jan. 8, 2021, 1 page.

English language abstract for EP 0 727 298 B1 extracted from espacenet.com database on Jan. 8, 2021, 1 page.

English language abstract for EP 1 146 185 A2 extracted from espacenet.com database on Jan. 8, 2021, 2 pages.

English language abstract for EP 1 146 185 A3 extracted from espacenet.com database on Jan. 8, 2021, 2 pages.

English language abstract for EP 1 146 185 B1 extracted from espacenet.com database on Jan. 8, 2021, 2 pages.

\* cited by examiner

PATIENT TRANSPORT APPARATUS WITH CRASH DETECTION

CROSS-REFERENCE TO RELATED APPLICATION

The subject application claims priority to and all the benefits of U.S. Provisional Patent Application No. 62/954,855, filed on Dec. 30, 2019, the disclosure of which is hereby incorporated by reference in its entirety.

BACKGROUND

Patient transport apparatuses, such as hospital beds, stretchers, cots, wheelchairs, and transport chairs facilitate care and transportation of patients. Conventional patient transport apparatuses include a base having wheels and a litter including a patient support surface upon which the patient is supported.

Some patient transport apparatuses are designed to be routinely loaded into and unloaded from an emergency transport vehicle, such as an ambulance. A fastening system may be employed in the transport vehicle to facilitate loading and unloading of the patient transport apparatus and/or to secure the patient transport apparatus in the transport vehicle. Occasionally, the transport vehicle may be involved in a crash event, such as when the transport vehicle collides with another vehicle or obstacle and is subjected to atypical forces—which can result in damage to the patient transport apparatus. It may be challenging to detect such crash events and/or to detect corresponding damage to the patient transport apparatus.

A patient transport apparatus that addresses one or more of the aforementioned challenges is desired.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION OF THE EMBODIMENTS

Figure 1:
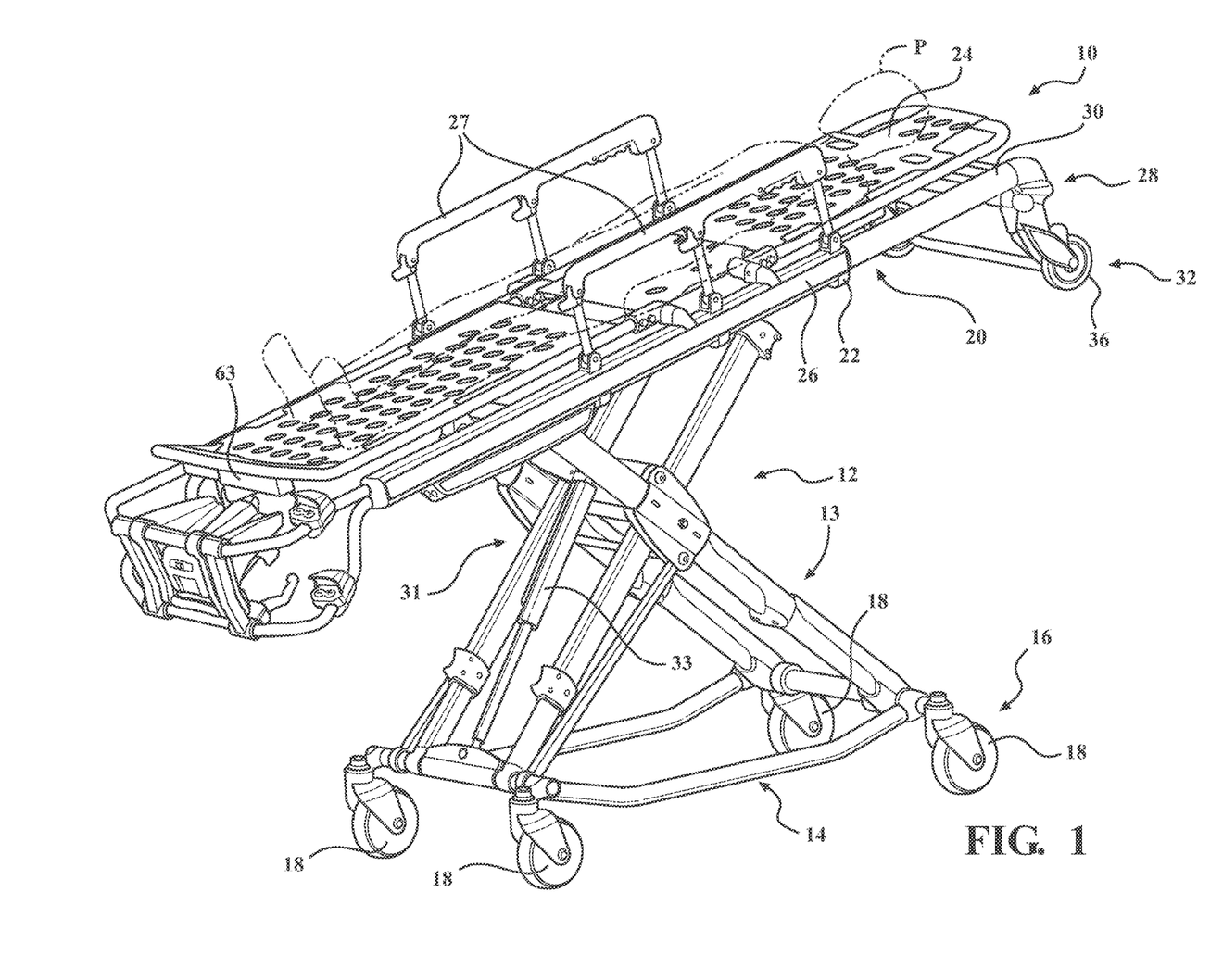
FIG. 1 is a perspective view of a patient transport apparatus.

Referring to FIG. 1, a patient transport apparatus 10 is shown for supporting a patient P in a variety of settings. The patient transport apparatus 10 illustrated in FIG. 1 is a cot. In other embodiments, however, the patient transport apparatus 10 may be a hospital bed, stretcher, wheelchair, transport chair, or similar apparatus utilized in the transportation, support, and care of a patient.

The patient transport apparatus 10 includes a support structure 12 to provide support for the patient. The support structure 12 includes a base frame 14. The base frame 14 may include longitudinally extending frame members and crosswise extending frame members interconnected at ends thereof to form a generally rectangular base frame. A plurality of caster wheel assemblies 16 with caster wheels 18 are operatively connected proximate each corner of the base frame 14. The caster wheels 18 may be configured to swivel to facilitate turning of the patient transport apparatus 10. One or more of the caster wheel assemblies 16 may include a brake to prevent rotation of its associated caster wheel 18 when engaged. One or more of the caster wheel assemblies 16 may also include a swivel locking mechanism to prevent its associated caster wheel 18 from swiveling when the swivel locking mechanism is engaged.

The support structure 12 further includes a support frame 13 and a litter 20 including a litter frame 22. The litter 20 includes a patient support deck 23, which may have one or more articulable sections, such as a back section and/or a foot section. The patient support deck 23 is supported by the litter frame 22. The patient support deck 23 defines a patient support surface 24 configured to support the patient P. The litter frame 22 may include frame rails 26 extending longitudinally (e.g., on one or both sides of the litter frame 22). The litter frame 22 may further include a retracting head section 28. The retracting head section 28 may include a pair of telescoping frame rails 30 (only one shown) that slide in and out relative to the frame rails 26 between a retracted position and an extended position or one or more positions in between (extended position shown in FIG. 1).

Side rails 27 may extend from opposing sides of the litter frame 22 to provide egress barriers for the patient P on the patient support surface 24. The side rails 27, along with other handles, may be utilized by an emergency medical technician or other medical professional, to manually move or manipulate the patient transport apparatus 10.

The support frame 13 is arranged to interconnect the base frame 14 and the litter 20 and may include a lift mechanism 31 to facilitate raising and lowering of the litter 20 relative to a transport surface (e.g., ground). The lift mechanism 31 may be manipulated to adjust the height of the litter 20 to a maximum height (see, e.g., FIG. 1), a minimum height, or any intermediate height in between the maximum and minimum heights. The lift mechanism 31 may include an actuator system including one or more actuators 33 configured to manipulate a pair of X frames to raise and lower the litter 20. Such a lift mechanism is described in U.S. Pat. No. 7,398,571, filed on Jun. 30, 2005, entitled, "Ambulance Cot and Hydraulic Elevating Mechanism Therefor," the entire disclosure of which is incorporated by reference herein. Other types of lift mechanisms may also be employed.

One or more loading wheel assemblies 32 may be coupled to the support structure 12. It should be appreciated that the loading wheel assemblies 32 may be connected to any suitable location on the patient transport apparatus 10, such as on the frame rails 30, on the patient support deck 23, connected to the base frame 14, or the like. In the embodiment shown, a pair of loading wheel assemblies 32 are connected to the retracting head section 28 and are movable in elevation relative to the caster wheel assemblies 16 via the lift mechanism 31. Each of the loading wheel assemblies 32 includes a loading wheel 36 to engage a floor surface 74, such as a deck of an emergency transport vehicle VEH (e.g., ambulance, helicopter, etc.), or to engage a fastening system 40 (see FIG. 2), or both. Ideally, the loading wheels 36 are positioned and configured to facilitate loading and unloading of the patient transport apparatus 10 into and out of the emergency transport vehicle VEH.

Figure 2:
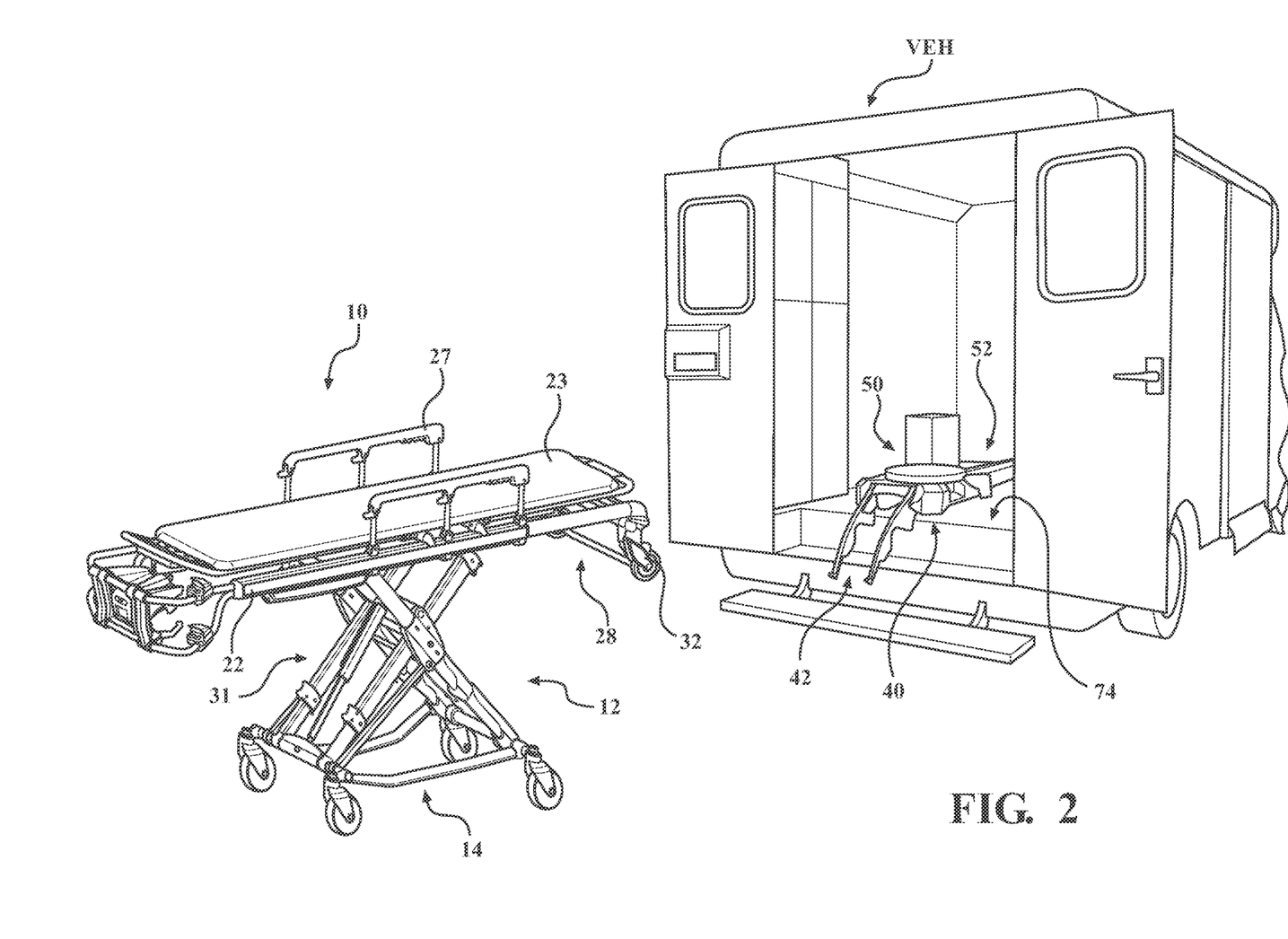
FIG. 2 is a perspective view of the patient transport apparatus approaching an emergency transport vehicle to be loaded into the transport vehicle.

FIG. 2 illustrates the fastening system 40 for loading the patient transport apparatus 10 into the transport vehicle VEH. The patient transport apparatus 10 is designed to be routinely loaded into and unloaded from the transport vehicle VEH. The fastening system 40 may further secure the patient transport apparatus 10 to the transport vehicle VEH to prevent movement during transportation. Various types and forms of fastening systems are contemplated and may be used to secure the patient transport apparatus 10 in the transport vehicle VEH. Fastening systems that can be used may be similar to those shown in U.S. Pat. No. 7,887,113, entitled, "Powered Patient Support And Fastening System With Inductive Based Power System," or U.S. Pat. No. 8,439,416, entitled, "Ambulance Cot And Loading And Unloading System," both of which are incorporated by reference herein.

In the illustrated embodiment, the fastening system 40 includes a loading and unloading device 42 that loads the patient transport apparatus 10 into, and unloads the patient transport apparatus 10 from, the transport vehicle VEH, as well as fastens the patient transport apparatus 10 in the transport vehicle VEH once the patient transport apparatus 10 is loaded into the transport vehicle VEH. When the patient transport apparatus 10 is fully loaded into the transport vehicle VEH, a vehicle power supply 44 may be employed to recharge a rechargeable power supply B1 of the patient transport apparatus 10 (see FIG. 3). Other forms of recharging systems or power supply arrangements are also contemplated.

Figure 3:
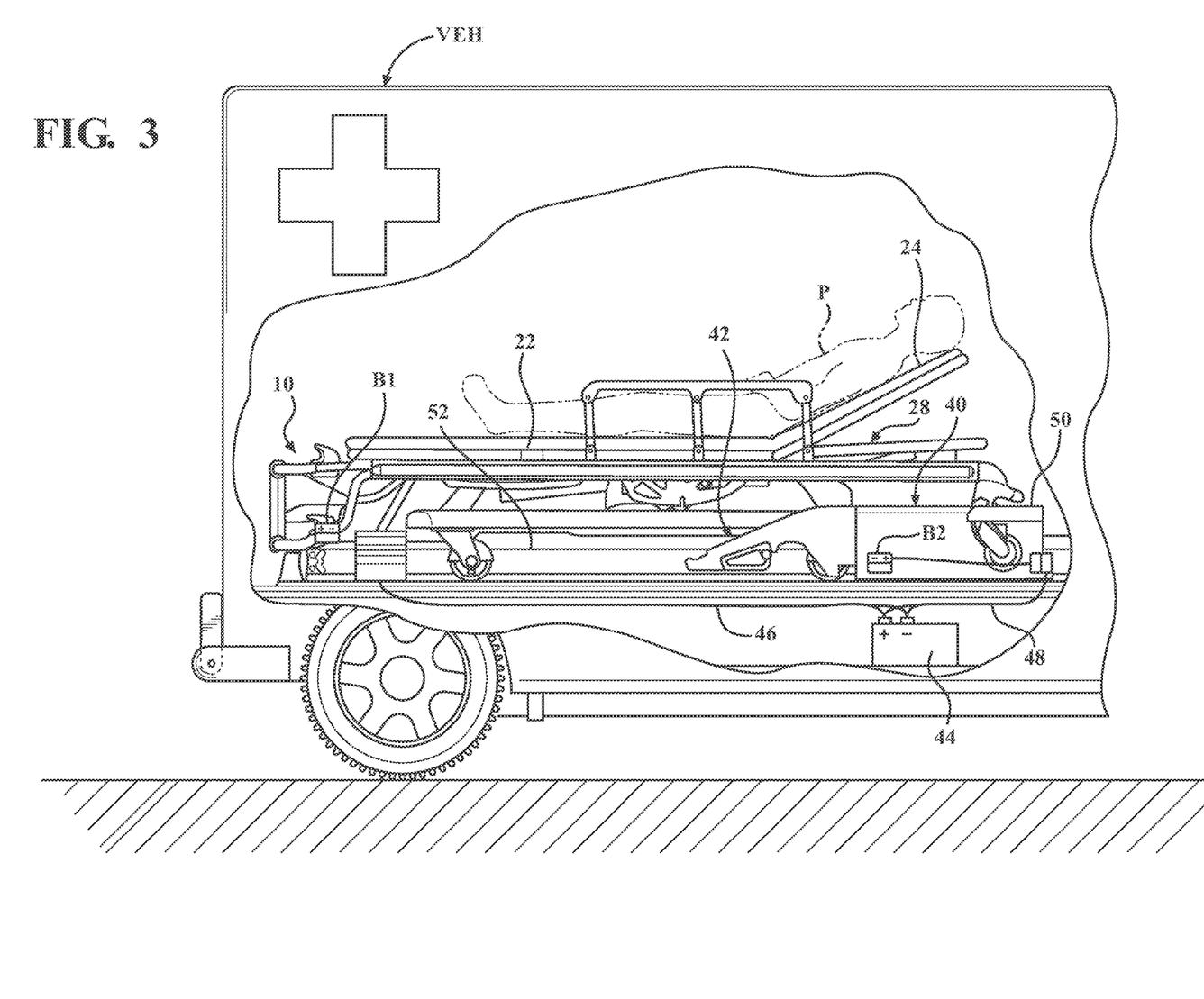
FIG. 3 is a schematic illustration of the patient transport apparatus loaded into the transport vehicle.

Referring to FIG. 3, the vehicle power supply 44 may include a conventional DC power supply or source, such as a battery, which is connected to two power supply circuits 46, 48 for recharging the rechargeable power supply B1 on the patient transport apparatus 10 and for recharging a rechargeable power supply B2 on the loading and unloading device 42. These power supply circuits 46, 48 may provide such recharging through wireless power transmission, namely by inductive coupling, as best described in U.S. Pat. No. 7,887,113, incorporated herein by reference. Wired power transmission is also contemplated. Wired and/or wireless data transmission between the patient transport apparatus 10 and the transport vehicle VEH are also contemplated, as described further below.

The loading and unloading device 42 includes a carriage or trolley 50, which is mounted on one or more tracks or rails 52, which are in turn mounted to the floor surface 74 of the transport vehicle VEH. In the illustrated embodiment, the carriage 50 is configured to engage and releasably couple to the head end of the patient transport apparatus 10 so that the patient transport apparatus 10 may be guided into the transport vehicle VEH by the loading and unloading device 42 manually. See again U.S. Pat. Nos. 7,887,113 and 8,439,416, incorporated herein by reference, which discuss loading and unloading of the patient transport apparatus 10 in detail.

Figure 4:
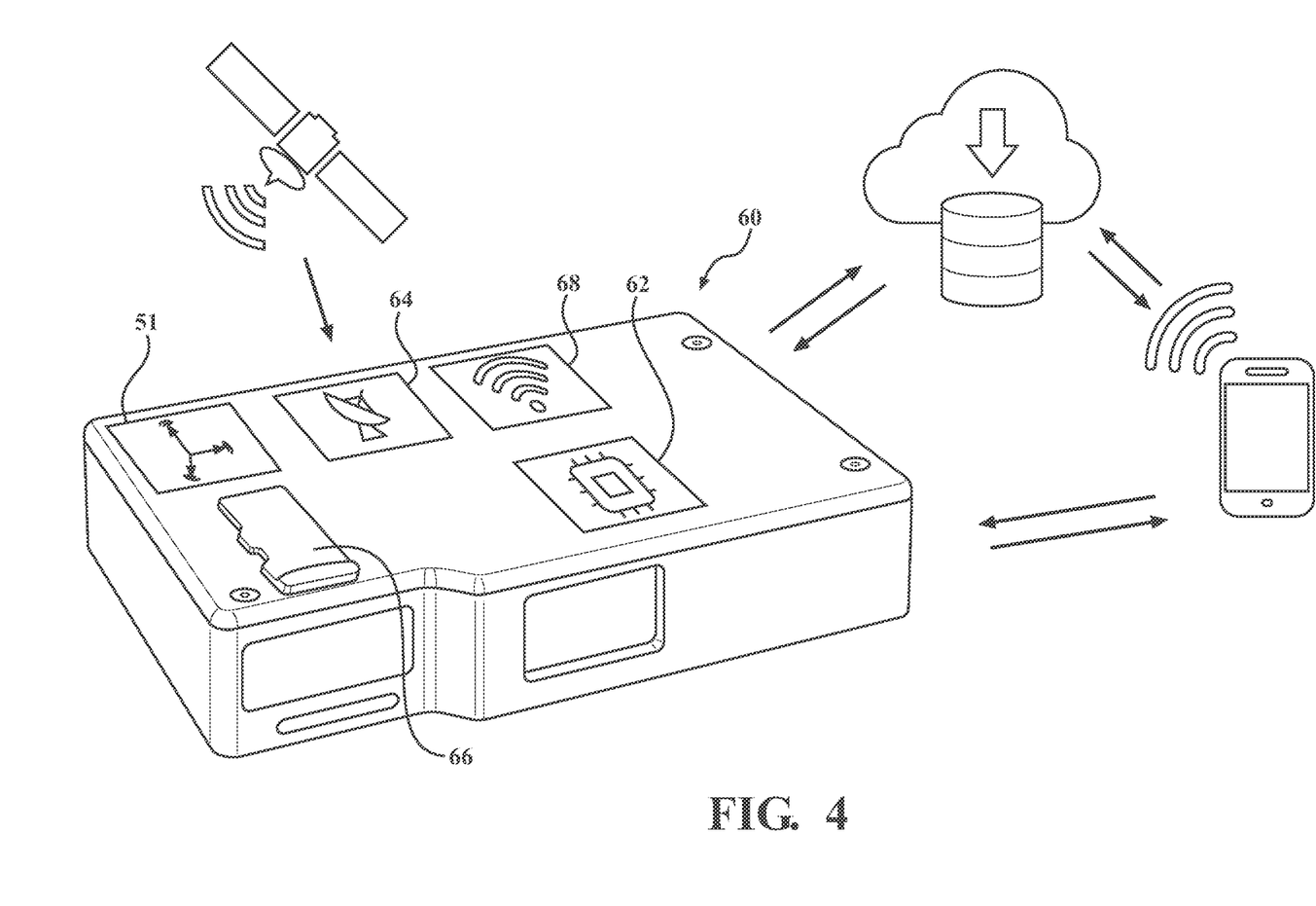
FIG. 4 is a schematic illustration of a control system and a controller for the patient transport apparatus.

Referring to FIG. 4, the patient transport apparatus 10 includes a control system 60 including a controller 62. The controller 62 may have one or more processors, microcontrollers, field programmable gate arrays, systems on a chip, discrete circuitry, suitable drivers, and/or other suitable hardware, software, or firmware that is capable of carrying out the functions described herein. The controller 62 may further comprise a non-transitory storage medium, such as memory 66, which may be configured to store data, as will be discussed in further detail below, and a program having instructions executable by the processor. The non-transitory storage medium may comprise one or more memory devices that may be removable and/or rewritable. For example, the controller 62 may comprise a first memory device mounted to a printed circuit board (PCB) and a second device (such as a microSD card), which may be removable from the controller 62. The controller 62 may be carried on-board the patient transport apparatus 10. In some implementations, the controller 62 may be mounted to the base frame 14. In other implementations, the controller 62 may be mounted to the litter 20, such as in an enclosure 63 mounted to the litter 20 (see FIG. 1). The controller 62 may be mounted at any suitable location on the patient transport apparatus 10. Power to the controller 62 and/or other electronic components described herein may be provided by the rechargeable power supply B1 and/or an external power source. The controller 62 may communicate with the other electronic components described herein via wired or wireless connections to perform one of more desired functions.

With continued reference to FIG. 4, the control system 60 may also include a location receiver 64, such as a satellite navigation receiver. For example, a Global Navigation Satellite System (GNSS) receiver for receiving location data usable for determining a location of the patient transport apparatus 10. Other suitable location receiver systems may comprise global or regional positioning systems such as GPS, GLONASS, BDS, and Galileo. The controller 62 may be configured to determine the location of the patient transport apparatus 10 within an accuracy of +/−100 m or other suitable accuracy. The location receiver 64 may be attached to the base frame 14, litter 20, or any other suitable location, and is in wired and/or wireless communication with the controller 62. The location receiver 64 may periodically receive location data, to update the location of the patient transport apparatus 10 at a predetermined interval (e.g. every minute) or may receive location data nearly continuously (e.g. 1 hz or 10 hz) to update the location of the patient transport apparatus more frequently. The location data may be converted into National Marine Electronics Association (NMEA) format and transmitted to the controller 62 via I2C/SPI/UART, or other suitable communication protocol. The controller 62 parses the location data to get coordinates (e.g., latitude and longitude) and stores the coordinates in the memory 66 of the control system 60. The location data also contains date/time data associated with the coordinates, e.g., timestamps. The controller 62 may also include a separate real-time clock to log date/time data and associate the date/time data with the location data. The location data (including coordinates) and date/time data can be used for detecting a location of the patient transport apparatus 10 over time, measuring a velocity of the patient transport apparatus 10, error logging, data logging, diagnostics, or the like.

The location data, date/time data, and identification data (e.g., a unique serial number or other unique identifier of the patient transport apparatus 10) can be transmitted from the controller 62 to a communication module 68 in wired and/or wireless communication with the controller 62, such as a USB, Wi-Fi or cellular module or other suitable communication module that is configured to transmit/receive data. When the communication module 68 connects to a network (e.g., internet, etc.), the location data, date/time data, and identification data can be transmitted to a server (e.g., cloud, etc.) for access by interested persons, such as owners, manufacturers, etc. of the patient transport apparatus 10. The location data, date/time data, and/or identification data, may be used for asset tracking of the patient transport apparatus 10 by service technicians or others to be better prepared prior to preventive maintenance.

While transporting the patient transport apparatus 10 (with or without the patient P), the transport vehicle VEH may be involved in a crash event (e.g., collision with another vehicle, collision with other objects, roll-over, etc.). In such a crash event, the patient transport apparatus 10 may be subjected to atypical forces due to accelerations (including decelerations) in one or more directions. The controller 62, by virtue of its connection to the location receiver 64 and memory 66 may be programmed to collect crash event data relating to such forces, along with the location data, date/time data, and/or identification data and to store these data in an event log for later review. Other data may also be collected, including data associated with the patient, the transport vehicle VEH, or the like.

One or more sensors may be mounted to the patient transport apparatus 10 and in communication with the controller 62 to detect crash events and generate crash event data. Such sensors may include accelerometers, inertial sensors, gyroscopes, pressure sensors, infrared sensors, ultrasonic sensors, optical sensors, encoders, or the like. The one or more sensors may be mounted to the base frame 14, the litter 20, or to any other suitable location to determine if the transport vehicle VEH has experienced a crash event. In some versions, the one or more sensors include an inertial sensor S1 coupled to the support structure 12. The inertial sensor S1 is configured to generate a signal representing a change in velocity (i.e. acceleration) of the support structure 12. The inertial sensor S1 may be mounted to the PCB onto which the controller 62, location receiver 64, memory 66, and communication module 68 are also mounted. The inertial sensor S1 may be aligned relative to the patient transport apparatus 10 such that its z-axis is aligned generally with a longitudinal axis of the patient transport apparatus 10, its y-axis is aligned generally with a vertical axis of the patient transport apparatus 10 (e.g., aligned to gravity), and the x-axis extends laterally. Other orientations of the inertial sensor S1 are also contemplated.

Figure 5:
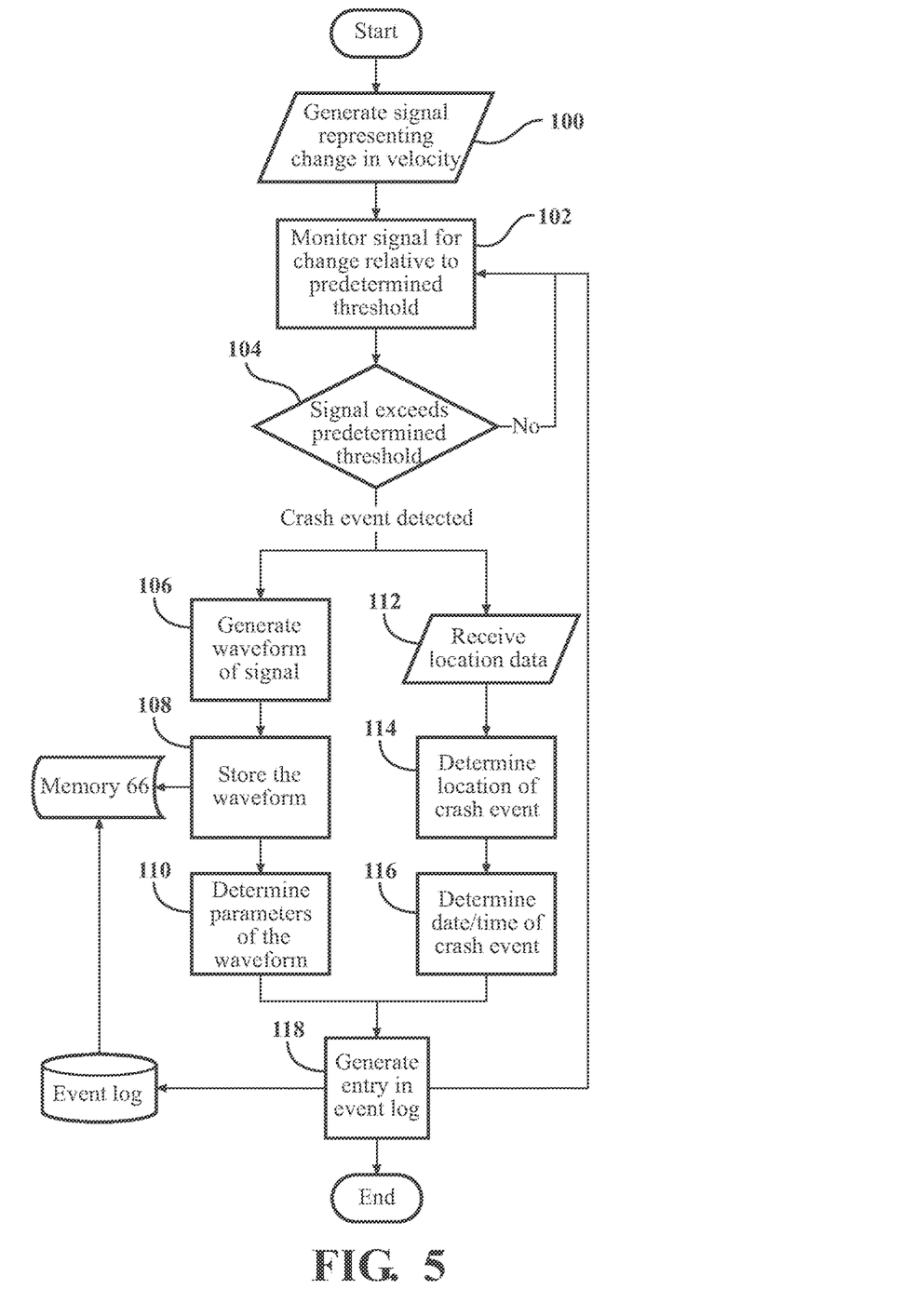
FIG. 5 is a flow diagram of steps carried out by the control system.

Referring to FIG. 5, in some methods, the controller 62 may detect that a crash event has occurred by monitoring the signal generated by the inertial sensor S1 for changes in velocity relative to a predetermined threshold. Said differently, the controller 62 identifies a crash event by comparing accelerations measured by the inertial sensor S1 to typical accelerations associated with normal transportation, such as typical accelerations associated with normal driving, including accelerations experienced when encountering speed bumps, potholes, hard braking, etc. More specifically, the inertial sensor S1 generates the signal representing the change in velocity in step 100, and in step 102 the controller 62 monitors the signal for a change relative to the predetermined threshold. In some versions, when the measured acceleration in any direction (e.g., along any of the x, y, z axes of a 3-axis accelerometer) reaches or exceeds a predetermined threshold, the controller identifies that a crash event may have occurred, see step 104. In some versions, a crash event occurs when a high acceleration is sustained over a period of time. For example, the predetermined threshold could be an acceleration value of 5 g (g-force) for 7 milliseconds (ms) along any of the x, y, z axes. In other words, this predetermined threshold would be met or exceeded if the measured acceleration along any axis was 5 g or more for at least 7 ms. Thus, the threshold may have acceleration and/or time values that must be met or exceeded. In some cases, the absolute value of the acceleration is compared to the threshold to identify crash events having a negative acceleration value that exceeds the predetermined threshold.

As mentioned above, in steps 102 and 104 the controller 62 detects that a crash event has occurred by monitoring the signal generated by the inertial sensor S1 for changes relative to the predetermined threshold. In response to an event in which the signal exceeds the predetermined threshold, a program stored on the memory 66 of the controller 62 is configured to capture and store/save the crash event data associated with the crash event from the inertial sensor S1 and other sensors to an event log in steps 106-118. The crash event data may include measured/calculated accelerations or velocities of the patient transport apparatus 10, measured/calculated forces, etc. Location data (e.g., from the location receiver 64) is received in step 112, and in step 114 the location of the crash event is determined. In some implementations of the patient transport apparatus 10, the velocity may be calculated using the location data, the data from the inertial sensor S1, and combinations thereof. Date/time data (e.g., from the location receiver 64 and/or the real-time clock) is captured in step 116.

As mentioned above, the crash event data associated with a crash event is stored in the event log, which is stored in the memory 66. More specifically, an entry is generated and added to the event log for each crash event. The entry comprises the crash event data from the associated crash event. As will be discussed in further detail below, the event log and each of the entries may be stored at an overwritable address in the memory 66.

The date/time data and location data are associated with the crash event data and logged in the memory 66 in step 118, and may further be transmitted to the network immediately or when the patient transport apparatus 10 is again connected to the network via the communication module 68—at which time the crash event data, date/time data, and location data is associated with the unique identification data. Of course, the crash event data, date/time data, and location data may be associated with the identification data at any point and may be stored with the identification data in the memory 66 for later retrieval. For example, the identification data may be stored as a parameter in each entry in the event log, or alternatively the identification data may be associated with the event log whereby each entry is associated with the identification data by virtue of the event log. The identification data may provide the unique serial number or other unique identifier that identifies the patient transport apparatus 10 and may further include information regarding the type of fastening system used to secure the patient transport apparatus 10. For example, there may be wired and/or wireless communication between the patient transport apparatus 10 and the fastening system 40, as previously described. In this case, the fastening system 40 may transmit its own unique identification data to the patient transport apparatus 10 for including in the event log and storage in the memory 66.

In some versions, once the data is collected and saved in the memory 66, the data can be uploaded to the network and stored on a remote server via the communication module 68 and/or the data can be sent wirelessly to another network and/or even logged remotely. For example, the communication module 68 may have cellular communication capability and be able to automatically transmit any of the data to a cellular network, or elsewhere, such as to a personal electronic device (e.g., mobile phone, tablet, service tool, etc.) to alert a remote user that a crash event has occurred. The data may be automatically reported to the personal electronic device or may be transmitted upon receiving some user input on the patient transport apparatus 10 and/or upon receiving some user input on the personal electronic device.

The data may also be reported in response to a tool (e.g., a laptop computer or other service tool) being connected to the controller 62 to access the memory 66 and the stored/logged data. The controller 62 may also automatically connect to the network and one or more servers to upload the data to the one or more servers the next time the communication module 68 connects to another communication module (e.g., via Wi-Fi, Bluetooth, Zigbee, etc.), such as when a crashed transport vehicle VEH returns to its station and connects to the station's communication module (e.g., Wi-Fi). As will be discussed in further detail below, the data may also be automatically sent to a service technician to create a calendar entry in their electronic calendar to have them follow-up with the owner of the patient transport apparatus 10 to inquire about the crash event. Ultimately, the controller 62 captures/provides the data (e.g., crash event data, date/time data, location data, identification data) for either immediate or later viewing and analysis by any users that may have use of the data.

Figure 6:
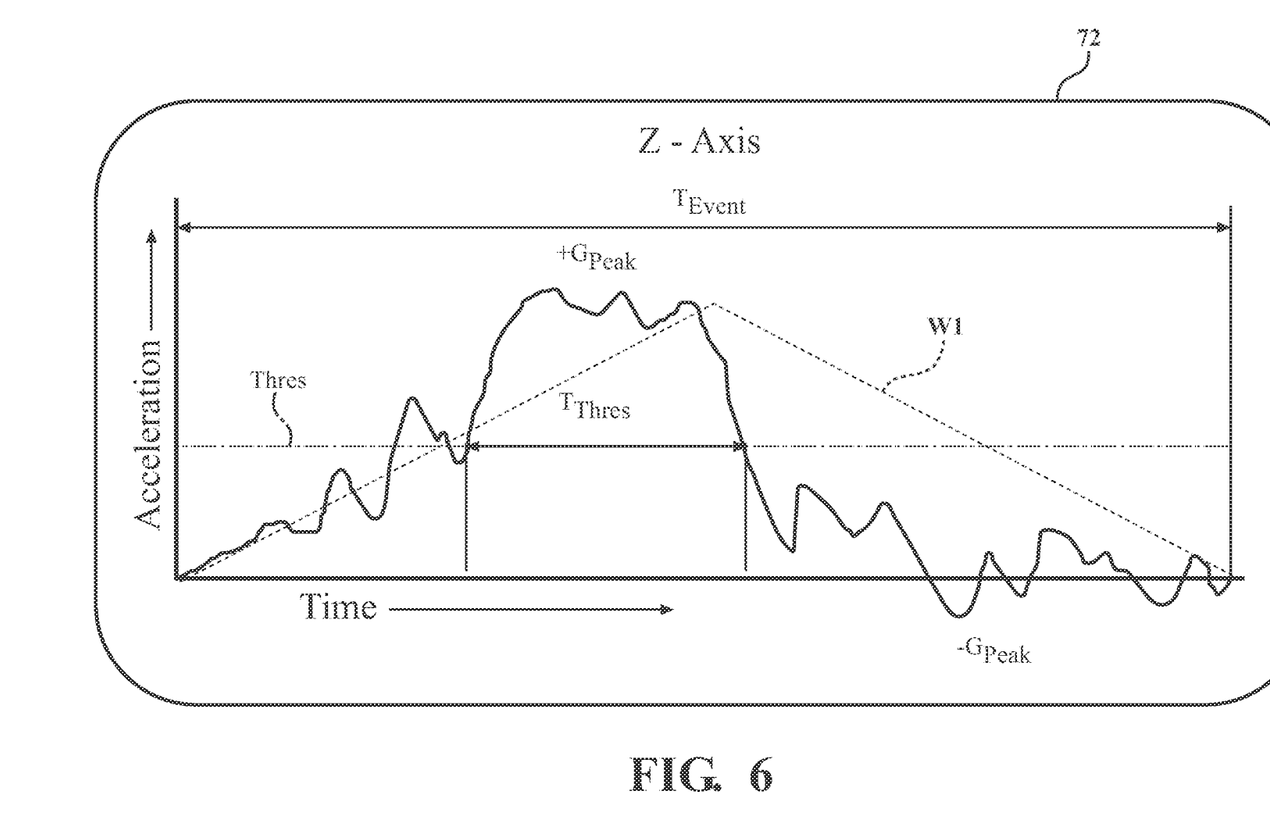
FIG. 6 is a graph of an acceleration waveform recorded by the control system.

Turning now to FIGS. 5 and 6, the crash event data generated by the controller 62 in response to a crash event may further include a waveform based on the signal received from the inertial sensor S1. More specifically, in step 106 the controller 62 generates a waveform of the signal received from the inertial sensor S1. The waveform may be a full profile (e.g., full waveform for each of the x, y, z axes) of measured acceleration over time during the crash event and/or during short periods of time before and/or after the crash event, e.g., 1 minute before and/or after the crash event. The waveform shown in FIG. 6 is for a single axis (in this case, the z-axis). Effectively, the inertial sensor S1 measures vibrations, accelerations, or the rate of change of velocity experienced by the patient transport apparatus 10 at any given time. The signal generated by the inertial sensor S1 may be processed to filter out smaller events like those associated with road bumps, hard braking, potholes, etc. As shown in FIG. 5, when acceleration values reaching and/or exceeding the predetermined threshold (i.e. associated with a crash event) are sensed, then the waveform data from the inertial sensor S1 is stored at an overwritable address in the memory 66 in step 108, which may include non-transitory memory, for the whole duration of the crash event. The controller 62 may also be programmed to continuously update (refresh) inertial sensor data in the memory 66, e.g., to always save the last few minutes of inertial sensor S1 data, so that when a crash event is detected, inertial sensor S1 data for the moments leading up to the crash event can be captured.

The crash event data assists in understanding the magnitude and duration of forces and impact experienced by the patient transport apparatus 10 during a crash event. In some versions, the memory 66 may have size limitations and/or the rechargeable power source B1 may have power limitations that makes logging all data impractical. As a result, the memory 66 may not hold all data for all crash events that the patient transport apparatus 10 has experienced over time. In these cases, a compressed set of data may be used that still provides meaningful insight about the impact of a crash event on the patient transport apparatus 10. For example, in step 110 the controller 62 may calculate/measure certain parameters during a crash event and log them in an entry in the event log stored in the memory 66 for every crash event, as opposed to storing a full profile of data for each crash event. In some cases, a full profile of data may be stored for a certain number of the most recent crash events, but only a partial profile of crash event data or certain parameters may be stored for previous crash events. For example, the controller 62 may determine the quantity of waveforms stored in the memory 66 using a counter (discussed below), and when the quantity exceeds a predetermined quantity or is expected to exceed an available allocation of the memory 66, each subsequent waveform would overwrite the oldest waveform stored in the memory 66. In a similar manner, some implementations of the controller 62 may have a limit to the quantity of entries that can be stored in the event log. The controller 62 may determine the quantity of entries in the event log using the counter, and when the quantity exceeds a predetermined quantity or is expected to exceed an available allocation of the memory 66, each subsequent entry would overwrite the oldest entry stored in the event log. It is further contemplated that instead of overwriting the oldest entry or waveform, the controller 62 could overwrite the least significant crash event based on one or more of the parameters.

Referring to FIG. 6, exemplary parameters that can be captured/calculated in step 110 based on the full profile may include:

$+G_{Peak}$—peak positive acceleration values observed during a crash event, captured and stored for each of the x, y, and z axes. The $+G_{Peak}$ value may be a peak magnitude value of acceleration in the positive direction of one or more of the component axes. The $+G_{Peak}$ value may further be a peak resultant magnitude and direction of the acceleration.

$-G_{Peak}$—peak negative acceleration values observed during a crash event, captured and stored for each of the x, y, and z axes. The $-G_{Peak}$ value may be a peak magnitude value of acceleration in the negative direction of one or more of the component axes. The $-G_{Peak}$ value may further be a peak resultant magnitude and direction of the acceleration.

$T_{Event}$—duration of the entire crash event.

$G_{Event}$ (not shown)—average of absolute acceleration values during the entire crash event, calculated and stored for each of the x, y, and z axes. The $G_{Event}$ value may be an average magnitude value of the absolute value of the acceleration in the direction of one or more of the component axes. The $G_{Event}$ value may further be an average resultant magnitude and direction of the acceleration.

$T_{Thres}$—duration when the acceleration values of the crash event are above a threshold continuously, calculated and stored for each of the x, y, and z axes. The $T_{Thres}$ value may further be the duration when the resultant acceleration values are above a threshold continuously.

$+G_{Thres}$—average of positive acceleration values when the acceleration is above the peak positive threshold continuously, calculated and stored for each of the x, y, and z axes. The $+G_{Thres}$ value may be an average magnitude value of acceleration in the positive direction of one or more of the component axes. The $+G_{Thres}$ value may further be an average resultant magnitude and direction of the acceleration.

$-G_{Thres}$—average of negative acceleration values when the acceleration is above (more negative) the peak negative threshold continuously, calculated and stored for each of the x, y, and z axes. The $-G_{Thres}$ value may be an average magnitude value of acceleration in the negative direction of one or more of the component axes. The $-G_{Thres}$ value may further be an average resultant magnitude and direction of the acceleration.

For each of the previous crash events, one or more of these parameters, and/or similar parameters, along with the associated date/time data (indicating the date/time of the crash event), and location data (indicating where the crash event occurred) can be combined and stored as an entry in the event log in step 118. Additionally, each of the waveforms may be assigned a unique ID, which is included in the corresponding entry in the event log. The controller 62 can also provide a counter that counts the number of crash events that have occurred, counts how many times the patient transport apparatus 10 has experienced an acceleration above a certain threshold, and/or provides other types of counts. For example, the controller 62 may be configured to receive service information from someone (e.g., a service technician, owner, manufacturer, etc.) and log service events, such as inspections or repairs, as entries in the event log.

Some implementations of the controller 62 may store the historical crash event data as entries in the event log stored in the memory 66, while a full profile of the most recent crash events are also stored. This provides a user with the full picture of the most recent crash events, but in the event that the amount of crash event data approaches a maximum capacity of the memory 66, at least certain data for all crash events will be stored, which allows someone (e.g., a service technician, owner, manufacturer, etc.) to see how frequently a particular patient transport apparatus 10 is exposed to crash events of similar (or different) intensity.

As mentioned above, the controller 62 and the communication module 68 may be configured to transmit the waveform and at least a portion of the event log to a user as well as a notification or calendar entry for a user (such as a service technician) to follow up or inspect the patient transport apparatus 10. The controller 62 may be further configured to calculate a damage rating, which may be based to one or more of the parameters of the entry. In some implementations, the damage rating may represent a relative severity of the crash event or may be an estimation of a service life of the patient transport apparatus 10. Said differently, the damage rating may be an arbitrary value that represents the integrity of the patient transport apparatus 10. Alternatively, the damage rating could represent a fatigue life for the patient transport apparatus 10. In one example the damage rating may be used to determine maintenance intervals of the patient transport apparatus 10, once a certain damage rating has been reached the controller 62 may notify a user that the patient transport apparatus 10 must be serviced. As mentioned above, service events may be logged, which may reset or lower the damage rating. In some implementations, the controller 62 may be configured to indicate that the damage rating has exceeded an allowable limit and the patient transport apparatus 10 must be replaced.

Of course, in some implementations that may have a greater amount of memory 66, a full profile of all crash events (e.g., full waveforms like that shown in FIG. 6) can be collected and stored over time for the entire life of the patient transport apparatus 10. This data can be associated with the date/time data and location data in the event log to provide a complete history of the accelerations and associated forces experienced by the patient transport apparatus 10. For example, the unique ID of each waveform may be used to recall the associated entry in the event log and vice-versa. However, even when only partial profiles/parameters are stored, this information still indicates to users how many crash events have been experienced by the patient transport apparatus 10, the intensity of those crash events (e.g., peak values, etc.), durations of the crash events, and can provide users with useful information regarding repair, maintenance, etc.

Other variations on the data captured/stored for crash events is also possible. For example, once a crash event is detected, all data for the crash event can be stored or only a subset of the data for the crash event can be stored—also data for the entire duration of the crash event could be stored, or only select portions of the duration of the crash event could be stored. The amount of data stored could depend on a selected sampling frequency for the inertial sensor S1 or other components, which may be adjustable by the user or manufacturer. In some variations, only a single parameter for the crash event is stored, or two or more parameters for the crash event are stored, and such parameters may be based on: (i) data captured for the entire crash event (e.g., inertial sensor data); (ii) data captured for a portion of the crash event; (iii) data captured at selected intervals; and/or (iv) combinations thereof. Moreover, any combination of inertial sensor data (or other data) and/or parameters associated with such data could be stored for the entire crash event, any portion of the crash event, and/or combinations thereof, and various combinations of such data and/or parameters could be captured, calculated, and/or stored for the current crash event and for any of the previous crash events.

During analysis of the data (including crash event data, date/time data, location data, and/or identification data, etc.) a full profile of a crash event from the patient transport apparatus 10 can be presented on a display 72 (see FIG. 6) of a computer or personal electronic device alongside (or overlaid onto) a standardized crash waveform W1 (e.g., on a screen of a laptop computer, mobile phone, tablet, scan tool used by a service technician, etc.). This can be done for the most recent crash event or any crash event for which data is stored in the memory 66. This provides a visual representation of the relativity of the crash intensity (e.g., to a service technician). For example, as shown in FIG. 6, the example standardized crash waveform W1 is shown. Standardized waveforms could be developed over time and correlated to those typical of causing at least some damage to the patient transport apparatus 10, or those typical of requiring service to the patient transport apparatus 10 (e.g., tightening fasteners, lubricating joints, etc.). As a result, by this comparison, the service technician or other person may be able to quickly ascertain the likelihood that some damage occurred or that service is necessary.

In some versions, data from a single crash event may be compared with the standardized waveform or data from multiple crash events can be compared, simultaneously. Furthermore, less than the full profile of data, e.g., a partial profile, could be compared to the standardized waveform, or any portion of the data, or any one or more of the parameters, could be compared to discrete thresholds to perform the analysis and determine if service is required. For example, if the $+G_{Peak}$ value exceeds a predefined threshold acceleration value, then this may indicate a need for service.

The information that can be displayed, includes, for example: (i) all or any portion of the stored data for a crash event or for any portion of the duration of a crash event (e.g., display data points at selected frequency); (ii) one or parameters stored for a crash event; (iii) the number of crash events over a given period of time (e.g., for the life of the patient transport apparatus 10); (iv) the intensity of the crash event; (v) the duration of the crash event; (vi) any other information associated with one or more crash events; (vii) and/or any combinations thereof.

In some versions, the crash event data, date/time data, location data, and/or other data may be captured and stored/logged only when the patient transport apparatus 10 is connected to and/or secured to the transport vehicle VEH, e.g., only when the patient transport apparatus 10 is secured in place via the fastening system 40. The patient transport apparatus 10 may comprise a sensor in communication with the controller 62 and configured to detect when the patient transport apparatus 10 is engaged with the fastening system 40 or secured to the transport vehicle VEH. As a result, forces experienced by the patient transport apparatus 10 in the field, i.e., when out of the transport vehicle VEH, can be ignored to help avoid incorrectly indicating that a crash event has occurred. Of course, such forces could also be captured and stored/logged in some embodiments. The controller 62 may further be configured to log whether the patient transport apparatus 10 was secured to the transport vehicle in each entry in the event log. In this way the crash event data can be sorted depending on whether the crash event occurred in a transport vehicle. In some embodiments, the data may only be captured and stored/logged when the rechargeable power supply B1 of the patient transport apparatus 10 is being charged by the charging circuit 46. In this case, power for the control system 60 may be provided by the rechargeable power supply B1 while charging, may be provided by the rechargeable power supply of the loading and unloading device 42, or may be provided by the vehicle power supply 44. Any suitable connections can be employed to provide power as needed. Further still, the controller 62 may be configured to identify and log the particular transport vehicle VEH that the patient transport apparatus was secured to when the crash event occurred.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient transport apparatus comprising:
a support structure comprising a base, a support frame, and a patient support deck defining a patient support surface to support a patient;
an inertial sensor coupled to the support structure and configured to generate a signal representing a change in velocity of the support structure;
a controller in communication with the inertial sensor and comprising a processor and a non-transitory storage medium having stored thereon a program that, when executed by the processor, is configured to:
monitor the signal generated by the inertial sensor for changes relative to a predetermined threshold, and
in response to an event in which the signal exceeds the predetermined threshold, the program is further configured to:
generate a waveform based on the signal received from the inertial sensor;
store the waveform at an overwritable address in the non-transitory storage medium; and
generate an entry in an event log stored in the non-transitory storage medium, the entry comprising one or more parameters associated with the waveform.

2. The patient transport apparatus of claim 1, wherein said entry overwrites an earlier entry in said event log when a quantity of entries in said event log exceeds a predetermined quantity.

3. The patient transport apparatus of claim 1, wherein said waveform overwrites an earlier waveform in said non-transitory storage medium when a quantity of waveforms stored in said non-transitory storage medium exceeds a predetermined quantity.

4. The patient transport apparatus of claim 1, further comprising a satellite navigation receiver configured to receive location data, and wherein said controller is configured to determine a location of said support structure using said location data.

5. The patient transport apparatus of claim 4, wherein said entry further comprises the location of said support structure during said event.

6. The patient transport apparatus of claim 4, wherein said controller is further configured to determine a speed of said support structure using said location data.

7. The patient transport apparatus of claim 6, wherein said entry further comprises the speed of said support structure during said event.

8. The patient transport apparatus of claim 1, wherein said entry further comprises a unique identifier for said waveform.

9. The patient transport apparatus of claim 1, wherein said parameters associated with said waveform include at least one of: a peak magnitude of an acceleration component, an average magnitude of an acceleration component, a peak magnitude and direction of acceleration, an average magnitude and direction of acceleration, a duration of said event, and a duration in which acceleration exceeds a predetermined threshold.

10. The patient transport apparatus of claim 1, wherein said controller further comprises a communication module configured to transmit said waveform and at least a portion of said event log.

11. The patient transport apparatus of claim 10, wherein said communication module is configured to receive service information and said program is further configured to generate a service entry in said event log.

12. The patient transport apparatus of claim 1, further comprising a sensor in communication with said controller and configured to detect when the patient transport apparatus is secured to a transport vehicle.

13. The patient transport apparatus of claim 12, wherein said entry further comprises whether the patient transport apparatus was secured to the transport vehicle during said event.

14. The patient transport apparatus of claim 1, wherein said program is further configured to calculate a damage rating based on said one or more parameters of said entries in said event log, wherein said damage rating corresponds to a service interval.

15. A method of logging event-specific data associated with movement of a patient transport apparatus, the method comprising:
generating a signal with a sensor coupled to a support structure of the patient transport apparatus, the signal representing changes in velocity;
monitoring the signal with a controller for a change relative to a predetermined threshold;
generating a waveform with the controller based on the signal in response to the signal exceeding the predetermined threshold;
generating an entry in an event log stored in a non-transitory storage medium of the controller, the entry comprising one or more parameters associated with the waveform; and
storing the waveform at an overwritable address in the non-transitory storage medium.

16. The method as set forth in claim 15, further comprising overwriting an earlier waveform in the non-transitory storage medium when a quantity of waveforms stored in the non-transitory storage medium exceeds a predetermined quantity.

17. The method as set forth in claim 15, further comprising receiving location data with a satellite navigation receiver coupled to the support structure, determining the location of the patient transport apparatus with the controller based on the location data, and storing the location in the entry in the event log.

18. The method as set forth in claim 17, further comprising determining the speed of the patient transport apparatus with the controller based on the location data and storing the speed in the entry in the event log.

19. The method as set forth in claim 15, further comprising transmitting at least a portion of the event log with a communication module of the controller to a remote device.

20. The method as set forth in claim 15, wherein the parameters associated with the waveform include at least one of: a peak magnitude of an acceleration component, an average magnitude of an acceleration component, a peak magnitude and direction of acceleration, an average magnitude and direction of acceleration, a duration of the waveform, and a duration in which acceleration exceeds a predetermined threshold.

* * * * *